US009566025B2

(12) United States Patent
Tsai et al.

(10) Patent No.: US 9,566,025 B2
(45) Date of Patent: Feb. 14, 2017

(54) IMAGE BASED OXYGEN SATURATION MEASURING DEVICE AND METHOD THEREOF

(71) Applicant: NATIONAL APPLIED RESEARCH LABORATORIES, Taipei (TW)

(72) Inventors: Hsin-Yi Tsai, Taipei (TW); Kuo-Cheng Huang, Taipei (TW); Yi-Ju Chen, Taipei (TW); Han-Chao Chang, Taipei (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 96 days.

(21) Appl. No.: 14/270,341

(22) Filed: May 5, 2014

(65) Prior Publication Data
US 2015/0313518 A1 Nov. 5, 2015

(51) Int. Cl.
*A61B 5/1455* (2006.01)
*A61B 5/00* (2006.01)

(52) U.S. Cl.
CPC .......... *A61B 5/1455* (2013.01); *A61B 5/14552* (2013.01); *A61B 5/68* (2013.01)

(58) Field of Classification Search
CPC ............ A61B 5/14555; A61B 5/14551; A61B 5/14552; A61B 5/68; A61B 5/6801
See application file for complete search history.

(56) References Cited

U.S. PATENT DOCUMENTS

| 4,880,304 | A | * | 11/1989 | Jaeb | A61B 5/14552 600/328 |
| 5,131,391 | A | * | 7/1992 | Sakai | A61B 5/14552 600/334 |
| 5,198,977 | A | * | 3/1993 | Salb | A61B 5/14553 600/310 |
| 5,566,673 | A | * | 10/1996 | Shiono | A61B 5/14553 600/476 |
| 5,853,370 | A | * | 12/1998 | Chance | A61B 5/0073 600/323 |
| 6,801,799 | B2 | * | 10/2004 | Mendelson | A61B 5/14552 600/322 |

* cited by examiner

*Primary Examiner* — Eric Winakur
(74) *Attorney, Agent, or Firm* — Chih Feng Yeh; Huntington IP Consulting Co., Ltd.

(57) ABSTRACT

The present invention is an image based oxygen saturation measuring device and method thereof. The method comprises steps of providing a plurality of red lights and a plurality of infrared lights arranged uniformly in an interlocked fashion and turned on alternatively; controlling the plurality of red lights and infrared lights to irradiate onto a selected skin area of a testee to have a red light turn-on period and an infrared light turn-on period; receiving a reflected version of the plurality of red lights and infrared lights from the selected skin area, respectively; and analyzing one reflected red light and one infrared light to acquire an oxygen saturation index for each of the coordination points. By means of the present invention, the measurement of oxygen saturation may be much exempted from effects brought from exterior interference and poor blood circulation, and may achieve a large measurement area in a single time.

15 Claims, 4 Drawing Sheets

IMAGE BASED OXYGEN SATURATION MEASURING DEVICE AND METHOD THEREOF

BACKGROUND OF RELATED ART

Technical Field

The present invention is related to an oxygen saturation technique, and particularly to an oxygen saturation measuring device and method.

Related Art

Oxygen concentration, also named as oxygen saturation, is crucial to human body health, some oxygen saturation measuring techniques are accordingly set forth, whereby achieving the purpose of disease prevention and monitoring.

An oximeter is a medical instrument measuring an oxygen containing amount in hemoglobin in human body. Dislike the measurement of blood collection/sampling, the oximeter does the measuring job based on non-invaded optical modulation mechanism, in which two optical beams having respective wavelengths which may be absorbed by oxyhemoglobin and deoxyhemoglobin in human body are provided for measurement. After the two optical beams transmit on a selected skin area with blood vessel below, a concentration of the oxyhemoglobin and deoxyhemoglobin may be measured respectively according to a variation from the incident light to the transmitted light.

The subject portion of the human body for the measurement may be a finger, a lobe, and a thigh. The transmitted light may be used as a basis for determining the oxygen saturation is because the intensity of incident light may be affected by the concentration of oxyhemoglobin and deoxyhemoglobin. Thereafter, the photoelectric conversion technique is used to acquire respective electric type signals of the oxyhemoglobin and deoxyhemoglobin. By means of computation conducted in the microprocessor, oxygen saturation equations defined previously in the microprocessor may calculate the oxygen saturation value.

Generally, the red light and infrared light are taken as the two light sources for measurement, and their wavelengths are 660 nm and 940 nm. In addition, the prior such device only uses a point light source for a single point of the skin for measurement. However, if the testee has a weak distal blood circulation, the obtained oxygen saturation information cannot exactly reflect the test's general oxygen saturation, and may not acquire the oxygen saturation information of other portions of the skin at one time. To obtain the oxygen saturation information for a specific area of the skin, the oximeter has to be used several times. However, one time of such measurement may only be conducted for a single point of the skin.

Typically, such prior device uses the transmitted light as the basis for determination of the output light intensity of the red light and infrared light. However, the transmitted light based measurement of oxygen saturation is apt to be affected by the lower blood amount, different skin colors, and irregular heart pulse. Therefore, the accuracy of such measurement needs to be promoted and verified. There has been a technique of determining the oxygen saturation by receiving a reflected red light and infrared light as the output lights, but the measured scope is still limited to a single point.

In view of the above, the prior oximeter still has to be improved to further satisfy the use of oxygen saturation measurement, and the present invention discloses accordingly an image oxygen saturation measurement device and method, whereby enhancing convenience and accuracy of the currently available such device.

SUMMARY

In view of the above, it is an object of the present invention to provide an image oxygen saturation measurement device and method, which is based on reflected lights to obtain a better accuracy and an area-based measurement.

The image oxygen saturation measuring device according to the present invention comprises a light source unit, comprising a base assembly, a red light set comprising a plurality of red lights, and an infrared light set comprising a plurality of infrared lights disposed alternatively with respect to the plurality of red lights, the plurality of red lights and infrared lights uniformly on the base assembly to irradiate onto a selected skin area of a testee, and the selected skin area having a plurality of coordination points each associated with a corresponding one of the plurality of red lights and infrared lights; an operational/processing unit, controlling the plurality of red lights to turn on simultaneously and the plurality of infrared lights to turn on simultaneously to have a red light period and an infrared light period, with the red light period presenting before or after the infrared period; an image receiving unit, receiving a version of the plurality of red lights and infrared lights reflected from the selected skin area, respectively, an image analysis/computation unit, analyzing an intensity of one of the plurality of reflected red lights and one of the infrared lights corresponding thereto, respectively, to acquire an oxygen saturation index for each of the coordination points of the selected skin area, respectively, an oxygen saturation distribution diagram establishing unit, establishing an oxygen saturation distribution for the selected skin diagram, to finish an oxygen saturation measurement process.

The image oxygen saturation measuring method according to the present invention comprises steps of irradiating a red light set comprising a plurality of red lights and an infrared light set comprising a plurality of infrared lights alternatively and uniformly onto a selected skin area of a testee, the selected skin area having a plurality of coordination points; controlling the plurality of red lights to turn on simultaneously and the plurality of infrared lights to turn on simultaneously, the plurality of red lights turning on before or after the plurality of infrared lights turning on; receiving a version of the plurality of red lights and infrared lights reflected from the selected skin area, respectively, and analyzing an intensity of one of the plurality of reflected red lights and one of the infrared lights corresponding thereto, respectively, to acquire an oxygen saturation index for each of the coordination points of the selected skin area, respectively, and establishing an oxygen saturation distribution diagram for the selected skin area, to finish an oxygen saturation measurement process.

In preferred embodiments, a white object is served as a basis for determination of the incident intensity from the reflected intensity of red lights and infrared lights. The oxygen saturation measurement process is performed in a dark environment. The irradiated red lights and infrared lights each have their preferred incident angles. The reflected red lights and infrared lights are each acquired with a monochromatic camera. And a mechanism for establishing an oxygen saturation distribution diagram is provided.

By means of the device and method of the present invention, the oxygen saturation measurement may be more exempted from interference of any external optical signal and effect of human distal blood vessel, and may achieve a large measurement area in a single time.

BRIEF DESCRIPTION OF THE DRAWINGS

The invention will become more fully understood from the detailed description given herein below illustration only, and thus is not limitative of the present invention, and wherein.

DETAILED DESCRIPTION

Figure 1:
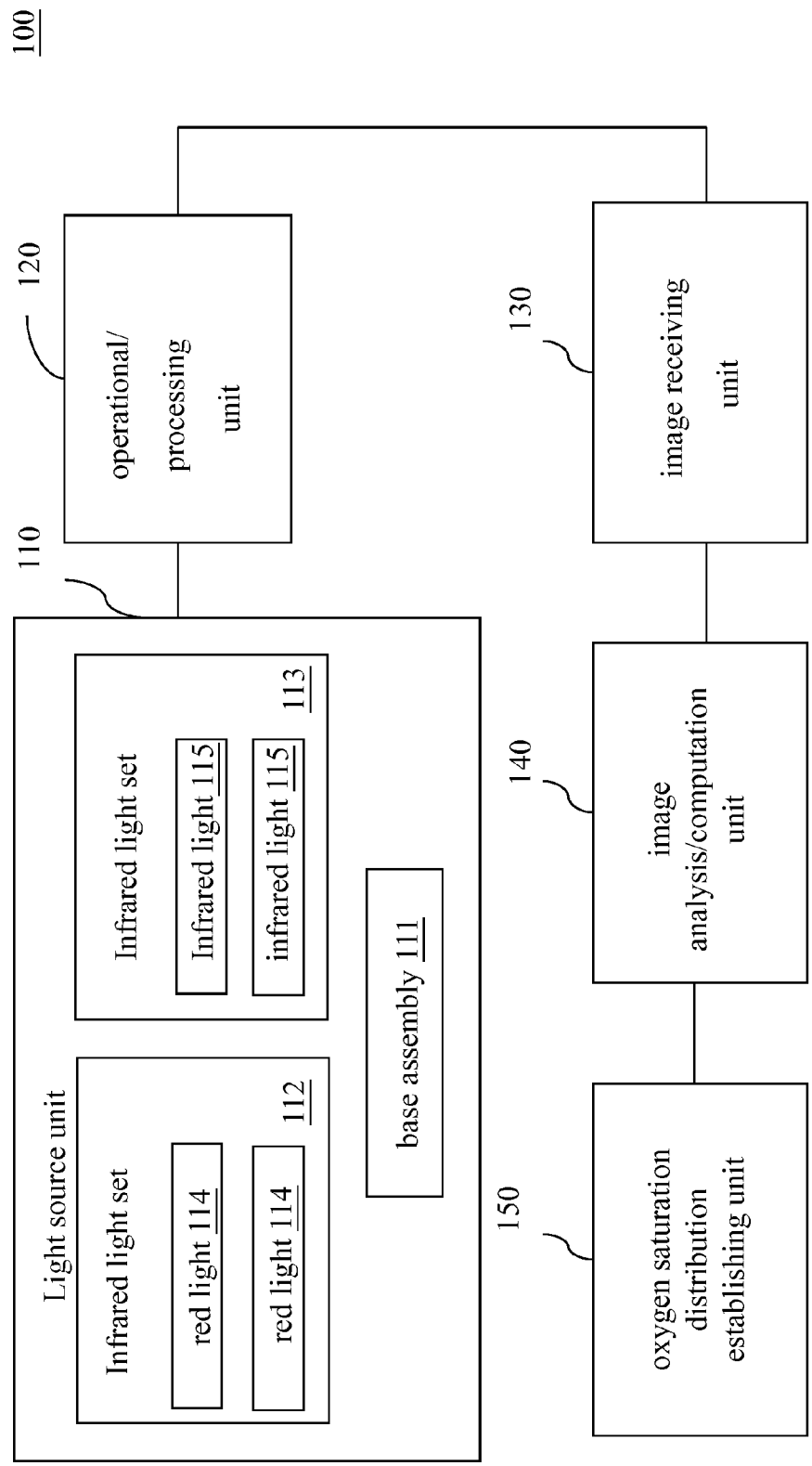
FIG. 1 is a block diagram of an image oxygen measurement device and method according to the present invention.

According to the present invention, the image oxygen saturation measuring device 100 comprises a light source unit 110, an operational/processing unit 120, an image receiving unit 130, an image analysis/computation unit 140, and an oxygen saturation distribution diagram establishing unit 150.

The light source unit 110 comprises a base assembly 111, a red light set 112 and an infrared light set 113. The red light set 112 comprises a plurality of red lights 114, and the infrared light set 113 comprises a plurality of infrared lights 115. In FIG. 1, the number of the red lights and infrared lights are both two, but this is merely an example, without limiting the present invention. The plurality of red lights are 114 disposed uniformly on the base assembly 111. Similarly, the plurality of infrared lights 115 are also disposed uniformly on the base assembly 111, presenting in an interloacked manner in arrangement with respect to the plurality of red lights 114, which may be further known by referring to FIG. 2.

Figure 2:
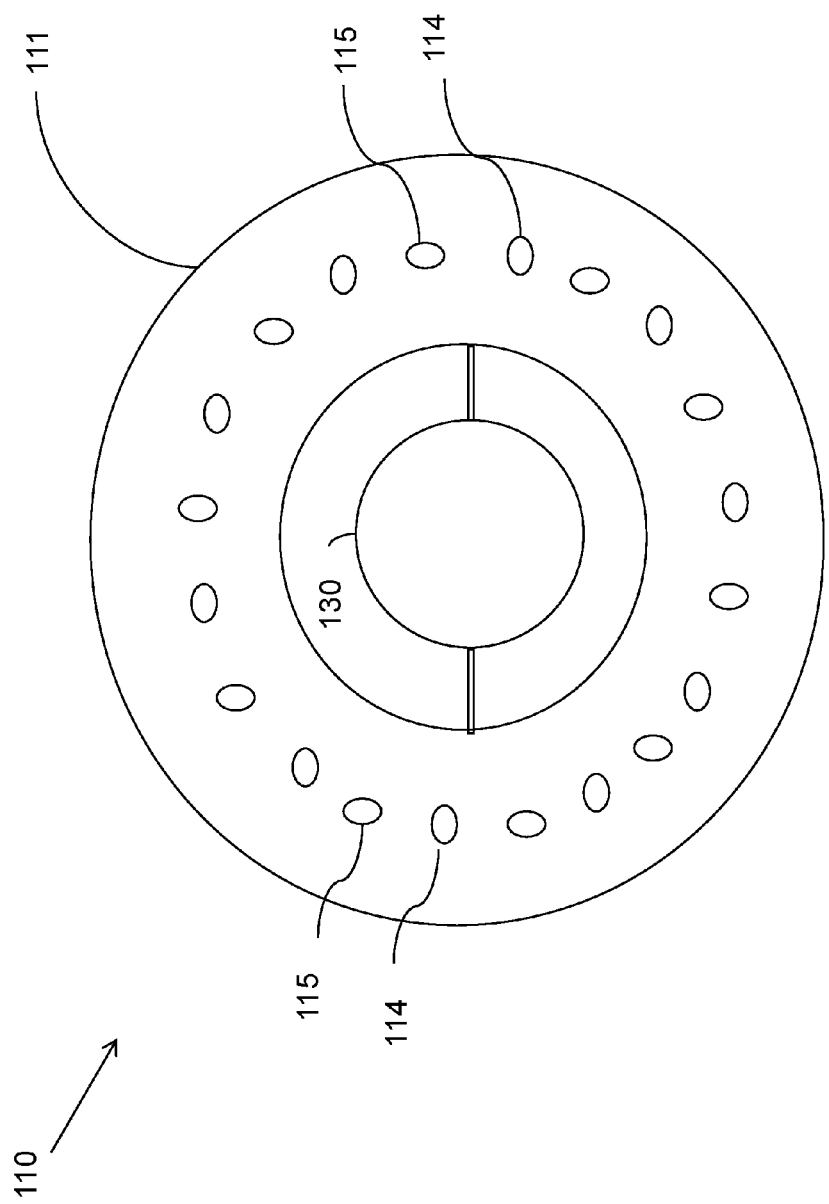
FIG. 2 is a diagram of a light source unit according to an embodiment of the present invention.

FIG. 2 is a diagram of the light source unit 110 according to an embodiment of the present invention. When the red lights 114 and the infrared lights 115 are turned on, red lights and infrared lights are emitted, respectively, to irradiate onto a selected skin area of a testee (now shown). On the selected skin area, a plurality of coordination points are defined, so that the plurality of red and infrared lights 114, 115 may be used for measuring oxygen saturation for each of such defined points on the selected skin area. In operation, each of the plurality of red lights and infrared lights is associated with a corresponding one of the plurality of red lights and infrared light. In FIG. 2, the base assembly 111 of the light source unit 110 is presented with a ring shape, and the plurality of red and infrared lights 114, 115 are disposed compliant with an along the ring shaped base assembly 111. However, the ring shape is merely an example, without limiting the present invention.

When the red and infrared lights 114, 115 enter into the skin, they will be reflected by a stratum corneum of the selected skin area, as will be later described and shown in FIG. 3, become diffused in a dermis of the selected skin area, as will be later described and shown in FIG. 3, thus forming an interference to a reflected version of the red and infrared lights, respectively. At this time, a wavelength of the red and infrared lights 114, 115 is selected as 660±20 nm and 890±20 nm, respectively, and an incident angle of the irradiated red lights and infrared lights is selected as 75±5°, respectively, to effectively exempt the reflected red light and infrared lights from the stratum corneum reflection and interference effect. In addition, to enable the red and infrared lights 114, 115 to uniformly irradiate on the select skin area, the light source unit 110 is disposed right above the selected skin area.

The operational/processing unit 120 is used to control the plurality of red lights 114 of the red light set 112 and the plurality of infrared lights 115 of the infrared light set 113 to turn on in turn, i.e. the red lights 114 are turned on simultaneously as a red light period before or after the infrared lights 115 are turned on as in infrared light period. In this manner, the red lights and the infrared lights may irradiate on the selected skin to perform the oxygen saturation measurement process.

The image receiving unit 130 is disposed right above the selected skin area and receives a version of the plurality of red lights 114 and infrared lights 115 reflected from the selected skin area, respectively. In an embodiment, the image receiving unit 130 is a monochromatic light receptor for further block any external light.

The image analysis/computation unit 140 analyzes a feature of the plurality of reflected red lights and infrared lights, respectively. As such, a comparison of each of the incident red lights 114 and each of the infrared lights 115 corresponding thereto may be used to acquire an oxygen saturation index of the coordination points of the selected skin area, respectively. In a preferred embodiment, the feature is an intensity. To avoid the received image to be affected by any external light, the provision of the red and infrared lights of the light source unit 110 and the reception of the reflected red lights and infrared lights are, in a preferred embodiment, performed in a dark environment.

Figure 3:
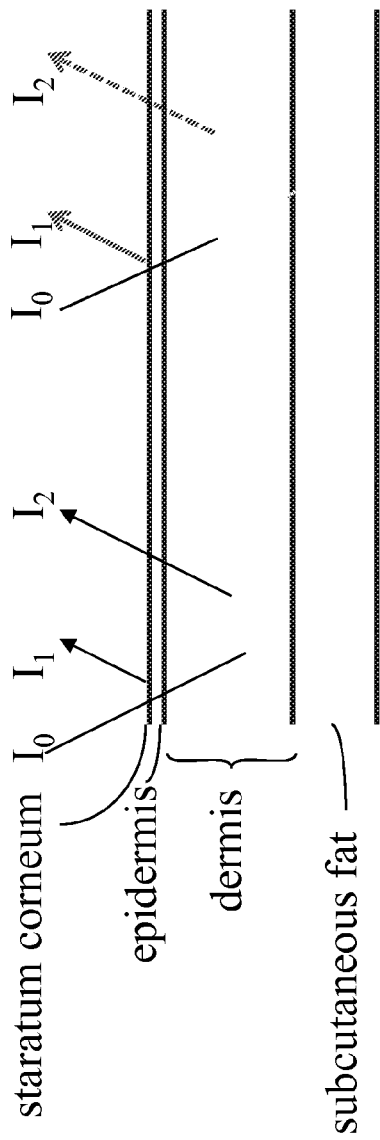
FIG. 3 is an illustration diagram explaining parameters regarding incident and reflected red light and infrared light according to the present invention.

Now referring to FIG. 3, which is an illustration diagram explaining parameters regarding incident and reflected red light and infrared light according to the present invention.

In the following, how the image analysis/computation unit 140 is operated to obtain the oxygen saturation index for all the coordination points within the selected skin area will be described with reference to FIG. 3.

FIG. 3 is an illustration diagram explaining parameters regarding incident and reflected red light and infrared light according to the present invention. The image analysis/computation unit 140 analyzes and calculates the oxygen saturation index for all the coordination points within the selected skin area by the following equations:

$$OD(\lambda) = \ln \frac{I_0 - I_1}{I_2 - I_1}, \quad (1)$$

$$R'(x, y) = \frac{(\varepsilon_{Hb}C_{Hb} + \varepsilon_{HbO_2}C_{HbO_2})_{\lambda=\lambda_1}}{(\varepsilon_{Hb}C_{Hb} + \varepsilon_{HbO_2}C_{HbO_2})_{\lambda=\lambda_2}} \quad (2)$$

$$= \frac{OD(\lambda_1) - k(\varepsilon_{water}C_{water} + \varepsilon_{other}C_{other})}{k[OD(\lambda_2) - \varepsilon_{water}C_{water} + \varepsilon_{other}C_{other}]}, \text{ and}$$

$$SpO_2 = \frac{C_{HbO_2}}{C_{Hb} + C_{HbO_2}} \quad (3)$$

wherein $\lambda$ is a light wavelength, OD is an intensity variation from an incident light to a reflected light corresponding thereto for each of the plurality of red lights and infrared lights, R' is a ratio of an optical absorption of an oxyhemoglobin and a deoxyhemoglobin for each of the plurality of red lights and the plurality of infrared lights, $\varepsilon$ is an optical absorption rate constant, $SpO_2$ is an oxygen saturation index, $HbO_2$ is the oxyhemoglobin, Hb is the deoxyhemoglobin, C is a material concentration, other is a material other than water and hemoglobin, k is a ratio of a transmission depth of each of the plurality of incident red lights and one of the plurality of infrared lights corresponding thereto, $I_0$ is the intensity of each of the plurality of incident red lights and infrared lights corresponding thereto, $I_1$ is the intensity of the plurality of reflected red lights and reflected infrared lights with respect to a stratum corneum of each associated with the coordination points of the selected skin area, and $I_2$ is the intensity of the plurality of reflected red lights and reflected infrared lights with respect to a dermis associated with each of the coordination points of the selected skin area.

In addition, it is to be noted that the parameter $I_1$ is related to the strautum corneum of the skin area and may vary with skin colors. After experiments performed for the present invention, it may be assured that the equation (1) is suitable to yellow race, and may be usable for other skin color people with some image correction mechanism. In addition, since the red light has a penetrating depth about 1.5 mm and the dermis has a thickness about 1 to 4 mm. Therefore, the measurement of oxygen saturation can be applied to the shallow skin layer.

In a preferred embodiment, the device 100 further comprises an oxygen saturation distribution diagram establishing unit 150, which may be selectively controlled by the operational/processing unit 120 to transform the obtained oxygen saturation index for all the coordination points within the selected skin area into an oxygen saturation distribution diagram. As such, the oxygen saturation distribution may be more directly known to a doctor and the testee.

In a preferred embodiment, the device 100 further comprises a white object, on which the red lights 114 and infrared lights 115 also irradiate, so that the intensity of the irradiated red and infrared lights may be determined with a common basis.

It is to be noted that the measurement conducted by the device 100 of the present invention may reach a measurement resolution up to 0.04 mm, which is known after experiment, but which does not limit the scope of the present invention.

Figure 4:
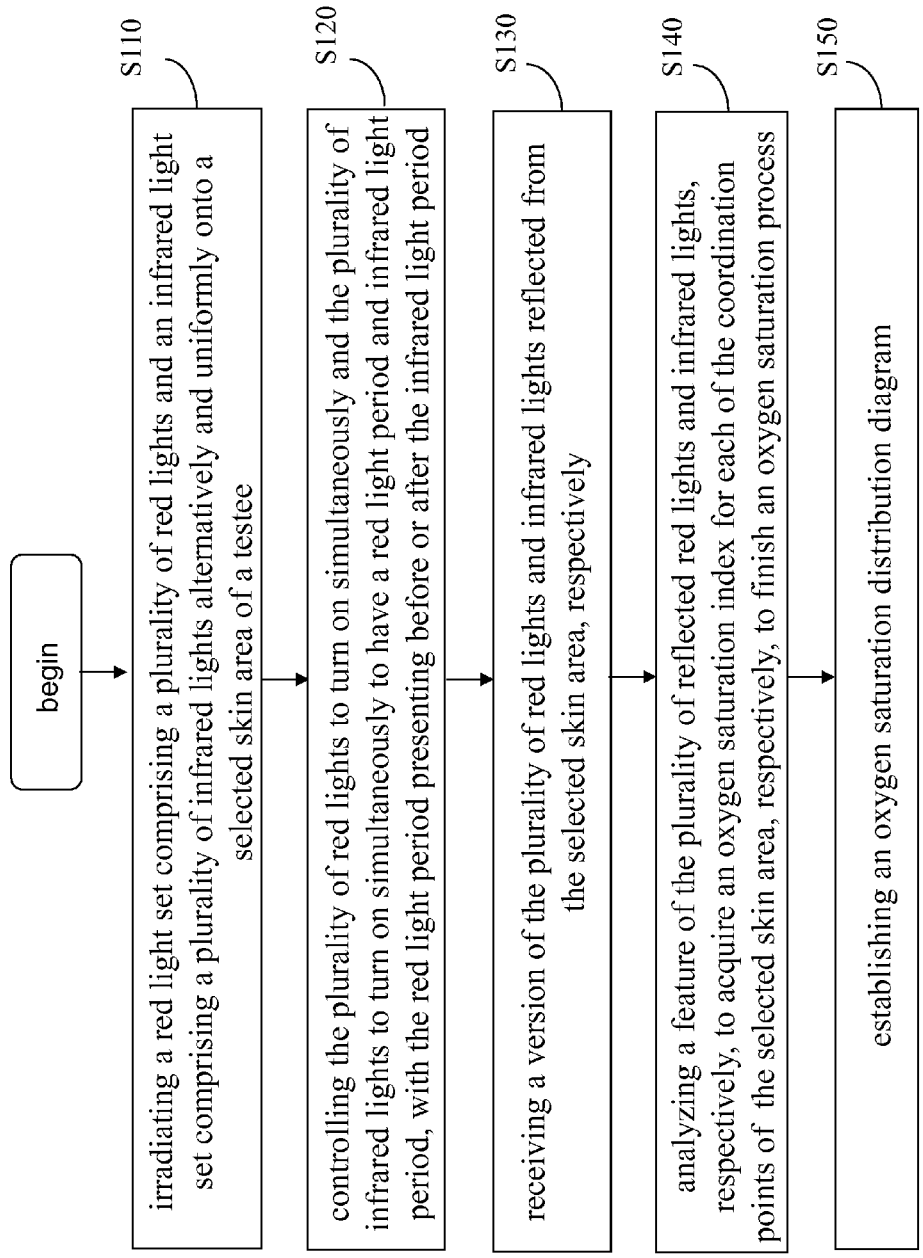
FIG. 4 is a flowchart diagram of an image oxygen saturation measurement according to the present invention.

Now referring to FIG. 4, which is a flowchart diagram of an image oxygen saturation measurement method according to the present invention.

The method is described in detailed as follows.

At first, irradiating a red light set comprising a plurality of red lights and an infrared light set comprising a plurality of infrared lights alternatively and uniformly onto a selected skin area of a testee (S110). The selected skin area has a plurality of coordination points, and each of which is associated with a corresponding one of the plurality of red lights and infrared lights, i.e. the coordination points and the red lights and infrared lights are presented in a one-to-one relationship. Then, controlling the plurality of red lights to turn on simultaneously and the plurality of infrared lights to turn on simultaneously to have a red light period and infrared light period, with the red light period presenting before or after the infrared light period (S120). Subsequently, receiving a version of the plurality of red lights and infrared lights reflected from the selected skin area, respectively (S130). Finally, analyzing an intensity of the plurality of reflected red lights and infrared lights, respectively, to acquire an oxygen saturation index for each of the coordination points of the selected skin area, respectively, to finish an oxygen saturation measurement process (S140). In step (S140), one of the plurality of reflected red lights and the one of the plurality of reflected infrared lights corresponding thereto are analyzed in a pair form to calculate a coordination point associated therewith, and each of the coordinate points within the selected skin area is subject to the process defined in step (S140).

In a preferred embodiment, the image oxygen saturation measuring method, further comprising a step of establishing an oxygen saturation distribution diagram (S150).

The red light has a wavelength of 660±20 nm, and the infrared light has a wavelength of 890±20 nm. Both of the irradiated red light and infrared light have an incident angle of 75±5°. Other descriptions for the method of the present invention are considerable with those for the above mentioned device of the present invention, and omitted here for clarity. For example, the resolution of the measurement of the present invention may reach up to 0.04 mm, without limiting the present invention. In addition, the step (S140) for analyzing and calculating the red lights and infrared lights and the reflective version thereof is performed by using the equations (1), (2) and (3).

In addition, the measurement of the present invention may have its selected skin area reaching up to 10 cm*10 cm.

By means of the present invention, the measurement of oxygen saturation may be much exempted from effects brought from exterior interference and poor blood circulation.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An image oxygen saturation measuring device, comprising:
    a light source unit, comprising a ring base assembly, a red light set comprising a plurality of red lights, and an infrared light set comprising a plurality of infrared lights disposed alternatively with respect to the plurality of red lights presenting in an interlocked manner in arrangement with respect to the plurality of red lights, the plurality of red lights and infrared lights uniformly on the ring base assembly to irradiate onto a selected skin area of a testee at a selected incident angle in the range of 75±5°, and the selected skin area having a plurality of coordination points each associated with a corresponding one of the plurality of red lights and infrared lights;
    an operational/processing unit, controlling the plurality of red lights to turn on simultaneously and the plurality of infrared lights to turn on simultaneously to have a red light period and an infrared light period, with the red light period presenting before or after the infrared light period;
    an image receiving unit, which is connected to the ring base assembly and being located in the center space of the ring base assembly, receiving a version of the plurality of red lights and infrared lights reflected from the selected skin area, respectively, and
    an image analysis/computation unit, analyzing a feature of one of the plurality of reflected red lights and one of the infrared lights corresponding thereto, respectively, to acquire an oxygen saturation index for each of the coordination points of the selected skin area, respectively, to finish an oxygen saturation measurement process.

2. The image oxygen saturation measuring device as claimed in claim 1, wherein the feature is an intensity.

3. The image oxygen saturation measuring device as claimed in claim 1, wherein the oxygen saturation measurement process is performed in a dark environment.

4. The image oxygen saturation measuring device as claimed in claim 1, further comprising an oxygen saturation distribution diagram establishing unit for establishing an oxygen saturation diagram for the selected skin area controlled by the operational/processing unit.

5. The image oxygen saturation measuring device as claimed in claim 1, wherein the image analysis/computation unit calculates the respective oxygen saturation of the plurality of coordination points according to equations as follows:

$$OD(\lambda) = \ln\frac{I_0 - I_1}{I_2 - I_1}, \quad (1)$$

$$R'(x, y) = \frac{(\varepsilon_{Hb}C_{Hb} + \varepsilon_{HbO_2}C_{HbO_2})_{\lambda=\lambda_1}}{(\varepsilon_{Hb}C_{Hb} + \varepsilon_{HbO_2}C_{HbO_2})_{\lambda=\lambda_2}} \quad (2)$$

$$= \frac{OD(\lambda_1) - k(\varepsilon_{water}C_{water} + \varepsilon_{other}C_{other})}{k[OD(\lambda_2) - \varepsilon_{water}C_{water} + \varepsilon_{other}C_{other}]}, \text{ and}$$

$$SpO_2 = \frac{C_{HbO_2}}{C_{Hb} + C_{HbO_2}} \quad (3)$$

wherein λ is a light wavelength, OD is an intensity variation from an incident light to a reflected light corresponding thereto for each of the plurality of red lights and infrared lights, R' is a ratio of an optical absorption of an oxyhemoglobin and a deoxyhemoglobin for each of the plurality of red lights and the plurality of infrared lights, E is an optical absorption rate constant, SpO2 is an oxygen saturation index, HbO2 is the oxyhemoglobin, Hb is the deoxyhemoglobin, C is a material concentration, other is a material other than water and hemoglobin, k is a ratio of a transmission depth of each of the plurality of incident red lights and one of the plurality of infrared lights corresponding thereto, I0 is the intensity of each of the plurality of incident red lights and infrared lights corresponding thereto, I1 is the intensity of the plurality of reflected red lights and reflected infrared lights with respect to a stratum corneum of each associated with the coordination points of the selected skin area, and I2 is the intensity of the plurality of reflected red lights and reflected infrared lights with respect to a dermis associated with each of the coordination points of the selected skin area.

6. The image oxygen saturation measuring device as claimed in claim 1, wherein each of the plurality of red lights has a wavelength of 660±20 nm, each of the plurality of infrared lights has a wavelength of 890±20 nm.

7. The image oxygen saturation measuring device as claimed in claim 1, wherein the selected skin area is up to 10 cm*10 cm.

8. An image oxygen saturation measuring method, comprising steps of:
irradiating a red light set comprising a plurality of red lights and an infrared light set comprising a plurality of infrared lights presenting in an interlocked manner in arrangement with respect to the plurality of red lights alternatively and uniformly onto a selected skin area of a testee at a selected incident angle in the range of 75±5° from a light source located on a ring base assembly, the selected skin area having a plurality of coordination points each associated with a corresponding one of the plurality of red lights and infrared lights;
controlling the plurality of red lights to turn on simultaneously and the plurality of infrared lights to turn on simultaneously to have a red light period and infrared light period, with the red light period presenting before or after the infrared light period;
receiving a version of the plurality of red lights and infrared lights reflected from the selected skin area, respectively, by an image receiver connected to the ring base assembly and being located in the center space of the ring base assembly and
analyzing a feature of one of the plurality of reflected red lights and one of the infrared lights corresponding thereto, respectively, to acquire an oxygen saturation index for each of the coordination points of the selected skin area, respectively, to finish an oxygen saturation measurement process.

9. The image oxygen saturation measuring method as claimed in claim 8, wherein the feature is an intensity.

10. The image oxygen saturation measuring device as claimed in claim 8, wherein the oxygen saturation measurement process is performed in a dark environment.

11. The image oxygen saturation measuring device as claimed in claim 8, wherein the step of receiving a version of the plurality of red lights and infrared lights reflected from the selected skin area respectively further comprises a step of receiving a monochromatic light component of the plurality of reflected red lights and reflected infrared lights from the selected skin area, respectively.

12. The image oxygen saturation measuring method as claimed in claim 8, further comprising a step of establishing an oxygen saturation distribution diagram for the selected skin area.

13. The image oxygen saturation measuring method as claimed in claim 8, wherein the step of analyzing the feature of the plurality of reflected red lights and infrared lights, respectively, to acquire an oxygen saturation index of the coordination points of the selected skin area, respectively, further comprises a step of calculating the respective oxygen saturation of the plurality of coordination points according to equations as follows:

$$OD(\lambda) = \ln\frac{I_0 - I_1}{I_2 - I_1}, \quad (1)$$

$$R'(x, y) = \frac{(\varepsilon_{Hb}C_{Hb} + \varepsilon_{HbO_2}C_{HbO_2})_{\lambda=\lambda_1}}{(\varepsilon_{Hb}C_{Hb} + \varepsilon_{HbO_2}C_{HbO_2})_{\lambda=\lambda_2}} \quad (2)$$

$$= \frac{OD(\lambda_1) - k(\varepsilon_{water}C_{water} + \varepsilon_{other}C_{other})}{k[OD(\lambda_2) - \varepsilon_{water}C_{water} + \varepsilon_{other}C_{other}]}, \text{ and}$$

$$SpO_2 = \frac{C_{HbO_2}}{C_{Hb} + C_{HbO_2}} \quad (3)$$

wherein λ is a light wavelength, OD is an intensity variation from an incident light to a reflected light corresponding thereto for each of the plurality of red lights and infrared lights, R' is a ratio of an optical absorption of an oxyhemoglobin and a deoxyhemoglobin for each of the plurality of red lights and the plurality of infrared lights, E is an optical absorption rate constant, SpO2 is the oxygen saturation index, HbO2 is an oxyhemoglobin, Hb is the deoxyhemoglobin, C is a material concentration, other is a material other than water and hemoglobin, k is a ratio of a transmission depth of each of the plurality of incident red lights and one of the plurality of infrared lights corresponding thereto, I0 is the intensity of each of the plurality of incident red lights and infrared lights corresponding thereto, I1 is the intensity of the plurality of reflected red lights and reflected infrared lights with respect to a stratum corneum of each associated with the coordination points of the selected skin area, and I2 is the intensity of the plurality of reflected red lights and reflected infrared lights with respect to a dermis associated with each of the coordination points of the selected skin area.

14. The image oxygen saturation measuring method as claimed in claim 8, wherein each of the plurality of red lights has a wavelength of 660±20 nm, each of the plurality of infrared lights has a wavelength of 890±20 nm.

15. The image oxygen saturation measuring method as claimed in claim 8, wherein the selected skin area is up to 10 cm*10 cm.

* * * * *